United States Patent [19]

Malette

[11] Patent Number: 5,423,780
[45] Date of Patent: Jun. 13, 1995

[54] THORAX DRAINAGE APPARATUS WITH VARIABLE VACUUM CONTROL

[76] Inventor: William G. Malette, 16461 Delate Rd., NE., Poulsbo, Wash. 98370

[21] Appl. No.: 303,777

[22] Filed: Sep. 9, 1994

[51] Int. Cl.6 .............................................. A61M 1/00
[52] U.S. Cl. ................................. 604/317; 604/118
[58] Field of Search .............................. 604/317–319, 604/118, 119; 251/205, 208; 137/205

[56] References Cited

U.S. PATENT DOCUMENTS

| | | | |
|---|---|---|---|
| 3,381,687 | 5/1968 | Andersen et al. | 128/276 |
| 3,463,159 | 8/1969 | Heimlich | 128/350 |
| 3,750,692 | 8/1973 | Tibbs | 137/205 |
| 3,757,783 | 9/1973 | Alley | 128/277 |
| 4,109,683 | 8/1978 | Strache | 251/205 |
| 4,112,948 | 9/1978 | Kurtz et al. | 128/276 |
| 4,289,158 | 9/1981 | Nehring | 137/205 |
| 4,439,189 | 3/1984 | Sargeant et al. | 604/317 |
| 4,468,226 | 8/1984 | Kurtz et al. | 604/318 |
| 4,481,008 | 11/1984 | Kurtz | 604/319 |
| 4,717,388 | 1/1988 | Steer et al. | 604/323 |
| 4,738,672 | 4/1988 | Malette | 604/319 |

FOREIGN PATENT DOCUMENTS 0096195  12/1983  European Pat. Off. .

Primary Examiner—Jerome L. Kruter
Attorney, Agent, or Firm—Zarley, McKee, Thomte, Voorhees & Sease; Dennis L. Thomte

[57] ABSTRACT

A collection chamber for fluids and a vacuum control device for drainage of the thorax is described. The collection chamber is provided with ports for the attachment of tubing extending from the chest cavity and for connection to a vacuum pump. Instead of using a water level control vacuum regulator this collection chamber uses a system of calibrated holes in the chamber. The vacuum is controlled by calibrating the size of the holes and selectively opening the holes in the chamber to control the force of the vacuum.

7 Claims, 3 Drawing Sheets

THORAX DRAINAGE APPARATUS WITH VARIABLE VACUUM CONTROL

BACKGROUND OF THE INVENTION

1. Field of the Invention

This invention relates generally to medical equipment used in thoracic medicine and more specifically to thorax drainage apparatuses.

2. Description of the Prior Art

It is necessary to drain air and fluid from the pleural space following operation or injury to organs within the thorax. If drainage of air and fluid from the pleural space is not sufficient, the lung will not be able to expand to fill the pleural space which may result in respiratory insufficiency or the development of infection. Many different types of drainage devices have been provided for draining the pleural space. One method of draining the pleural space is to insert a catheter into the chest with the distal end thereof sealed by a condom having the end removed, to a complicated system of up to five serially connected chambers having constricted connections. In the later systems, now the state of the art, a problem arises when there is a high volume air leak from the lung which is common in older patients with inherent lung disease. In such systems, high vacuum levels are required to remove such volumes of air. During normal respiration, a negative pressure is developed, with respect to atmospheric pressure, in the pleural space. This is the result of the lowering of the diaphragm and the increased volume of the chest with the rise of the rib cage during inspiration. The normal value of the negative pressure is 3.5–8.0 centimeters of water. The volume flow of air is governed by the Hagen-Poiseuille Law which states that for a given pressure gradient and tube length, the determinant of flow rate is the radius of the tube. Anesthesiologists are acutely aware of this and breathing circuits in anesthesia are maintained as large and short as possible. When a tube ends in an abrupt manner in a chamber, the flow is no longer laminar but becomes turbulent which introduces added resistance to flow. The length of the tube (or pathway) is also important when vacuum is applied.

According to the formula:

$$C = 12.1 \frac{D^3}{L}$$

Where
D is tube diameter
L is length of tubing pathway
C is air flow in Liters/Minute
For example:
L=2.5 ft. flow=28.9 L/min
L=4.5 ft. flow=14.5 L/min
L=10.0 ft. flow=7.2 L/min Therefore, the optimum removal of air through a chest drainage device will occur when the largest tubing diameter is combined with the shortest pathway from the pleural space to the vacuum outlet. In addition, a minimum of abrupt changes from laminar flow to turbulent flow should interrupt the pathway.

The prior art devices do not meet these criteria. The pathway is by a series of connected chambers each of which contributes turbulence. Tubing pathways are unnecessarily long and in some cases, constructions are utilized to control flow or pressure all of which makes high vacuum a necessity to remove a given volume of air. Since the normal negative pressure required to keep the lung inflated and allow normal respiration is low, high vacuum negates the normal respiratory efforts. High vacuum can trap the lung against the intra pleural catheter thus occluding the catheter making the catheter ineffective and resulting in collapse of the lung. In addition, high vacuum overcomes the attempt of the lung tissue to seal itself thus causing the air leaks to continue or to increase. In applicant's earlier U.S. Pat. No. 4,738,672, a thorax drainage apparatus is disclosed which represented a significant advance in the art. However, it is believed that the instant invention represents a significant improvement over applicant's earlier patent. The standard method of vacuum control for chest drainage devices is by means of a column of water which is open to the atmosphere by means of a tube immersed to a depth equal to the amount of vacuum desired such as disclosed in the '672 patent. When that amount of vacuum is exceeded, atmospheric air enters the chamber and bubbles to relieve the excess vacuum. While this simple and effective method has been used successfully in the relatively stable environment of the hospital, it does have a disadvantage in a mobile environment especially when rapid transport is necessary. In the '672 patent, a simple chest drainage device was described which was admirably suited for such use. The device of the instant invention completes the requirements of stability without the hazards of a water column.

SUMMARY OF THE INVENTION

A thorax drainage apparatus is described which comprises a collection chamber having a first port formed in the upper end thereof which is in communication with a vacuum pump so that a negative pressure is created within the collection chamber. The collection chamber also has a second port formed therein which is adapted to be connected to a catheter tube extending to the patient's chest. A first valve is operatively mounted on the second port which is open during the respiratory exhalation mode and which is closed during the respiratory inhalation mode. A vacuum control mechanism is located on the upper surface of the chamber. The vacuum control mechanism consists of a plurality of openings fixed within the upper surface of the chamber and a cover which fits over the openings. The cover has a hole formed through its surface and the cover is designed to move so an individual opening may be lined up under the hole of the cover. Lining up the hole of the cover over an opening in the chamber releases pressure within the chamber and controls the force of the vacuum. The openings are of varying diameters which enables the operator of the device to vary the force of the vacuum. The cover may either be a round cover which rotates the hole over the opening in the chamber, or a rectangular cover which slides back and forth to align the hole over the opening in the chamber. A third alternative design is discussed below.

The upper end of the vent tube is in communication with the atmosphere. An exhaust port is also formed in the upper end of the collection chamber and is normally closed by a flap valve. The flap valve permits communication between the upper interior of the collection chamber and the atmosphere when a predetermined positive pressure is reached within the collection chamber. A needle port or valve is mounted in the second port so that excess negative pressure in the catheter tubing may be relieved at times.

As stated previously, the level of vacuum or negative pressure within the collection chamber is regulated by the vacuum control mechanism. The vacuum control mechanism does not have to be attached to the upper surface of the chamber. A third alternative design is to create a plurality of openings in the chest catheter tube in the same manner as on the surface of the chamber. A hollow, cylindrical covering is placed over the openings in the catheter tube. The hollow, cylindrical covering has a hole formed through the surface. By rotating the hollow, cylindrical covering, an individual hole is aligned over an opening in the catheter tube.

In the event that the vacuum pump fails in the closed position, air from the lung could build up pressure in the chamber to such a level which could collapse the lung. To prevent such lung collapse, the second valve or exhaust valve opens when the pressure within the collection chamber is greater than atmospheric pressure.

It is therefore a principal object of the invention to provide a new and improved thoracic drainage system.

More specifically, it is an object of the invention to provide a simplified system which provides the widest and shortest pathway for the removal of air and fluid from the pleural space.

It is a further object of the invention to provide an apparatus of the type described which permits the removal of excess negative pressure in the drainage tubing.

It is yet a further object of the invention to provide an apparatus of the type described including means for relieving excess pressure in the collection chamber.

Still another object of the invention is to provide a thoracic drainage apparatus including a vacuum control mechanism in parallel with the main collection chamber.

These and other objects will be apparent to those skilled in the art.

DESCRIPTION OF THE PREFERRED EMBODIMENT

Figure 1:
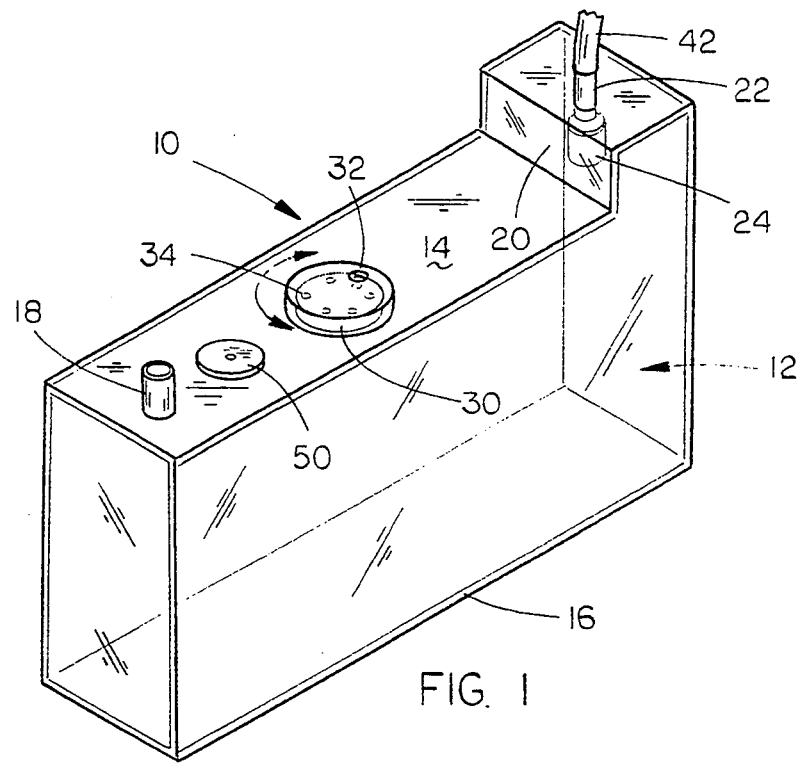
FIG. 1 is a perspective view of the apparatus of this invention.
Figure 2:
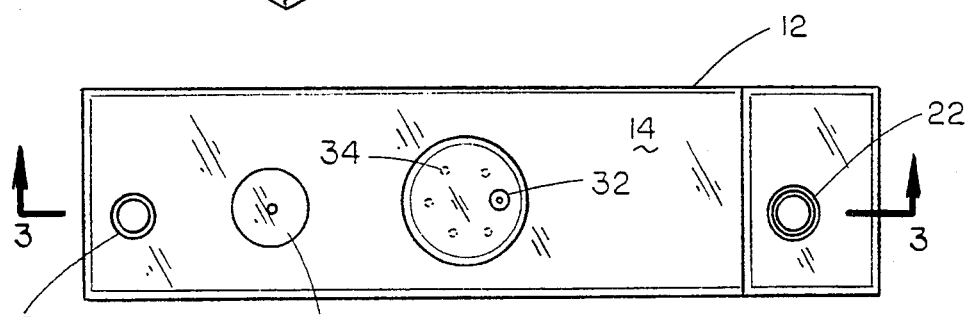
FIG. 2 is a top view of the apparatus of this invention.
Figure 3:
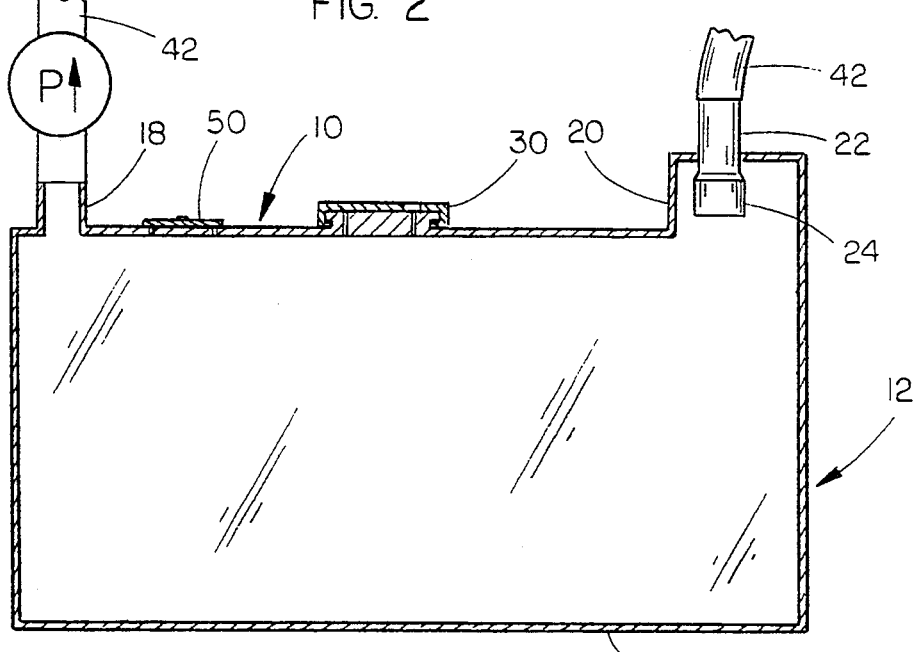
FIG. 3 is a longitudinal sectional view of the apparatus of FIGS. 1 and 2.

The thoracic drainage apparatus of this invention is referred to generally by the reference numeral 10 and includes a collection chamber or vessel 12 having an upper end 14 and lower end 16. Chamber 12 is provided with a port 18 provided at the upper end thereof which is adapted to be connected to a vacuum pump for creating a negative pressure within the collection chamber.

Collection chamber 12 is provided with an upper end portion 20 positioned at one end thereof. Mounted within upper end portion 20 is a port 22. The upper end of port 22 is connected to a drainage catheter tube extending from the pleural space within the chest. Port 22 has a valve means 24 mounted on the lower end thereof within upper end portion 20. Valve means 24 is of the "condom" type which is open during the respiratory exhalation mode but which is closed during the respiratory inhalation mode.

The thorax drainage apparatus 10 operates on the principle of creating a vacuum within the chamber 12 from an external source. The vacuum source draws air out of the chamber 12 through port 18 which has a catheter tube 42 connecting port 18 to the vacuum source. Pressure builds up within the chamber and draws in air through port 22. Port 22 also has a catheter tube attached to it which runs from port 22 to the pleural space within the chest. The vacuum draws fluids out of the pleural space within the chest and into collection chamber 12. As stated previously, valve means 24, mounted on the lower end of port 22, opens during respiratory exhalation but is closed during respiratory inhalation.

Figure 6:
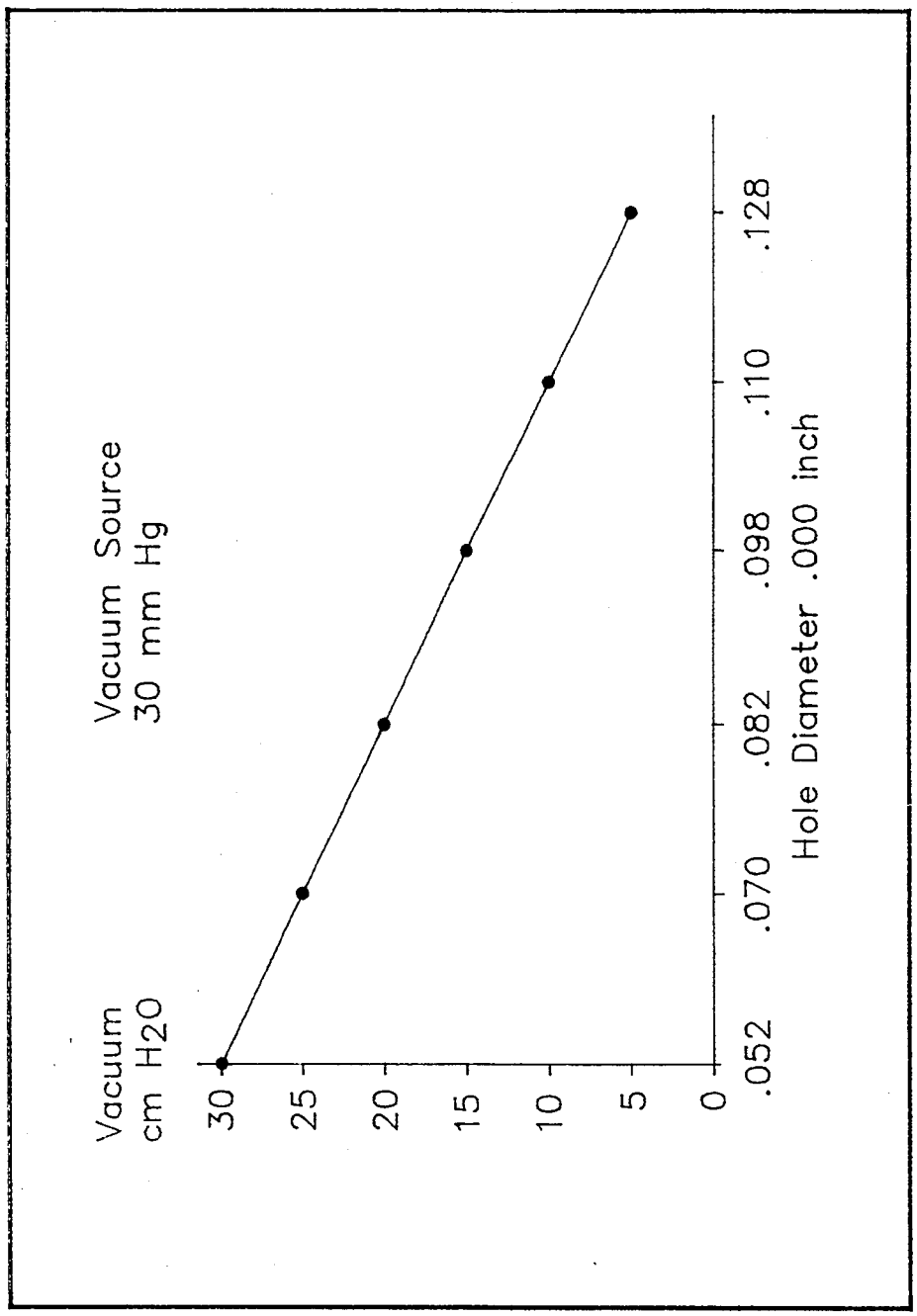
FIG. 6 is a chart illustrating the relationship of the strength of the vacuum in comparison to the diameter of the opening used.

It is very important to have the ability to vary the force of the vacuum when desired. This is accomplished by the vacuum control means. FIG. 1 illustrates one type of vacuum control means which is rotational vacuum control means 30. Rotational vacuum control means 30 is comprised of a flat, round disc with a circular hole 32 formed through the disc. The disc is affixed above a series of six openings 34 in the upper end 14 of the collection chamber aligned in a circle directly below the disc. Each opening 34 has a different diameter. The diameter of the six openings are 0.052, 0.070, 0.082, 0.098, 0.110 and 0.128 inches, respectively. Rotational vacuum control means 30 operates by rotating in place. This allows hole 32 to be lined up directly over any of the six openings 34. The operator of the draining apparatus controls the force of the vacuum inside the collection chamber 12 by rotating the rotational vacuum control means hole 32 over an opening 34 which gives the desired vacuum force. Aligning the vacuum control means hole 32 over an opening 34 with a large diameter would have the effect of lessening the vacuum force inside the collection chamber 12 to a greater extent than aligning hole 32 over an opening 34 with a small diameter opening. This is clearly illustrated in FIG. 6. An operator can manipulate the vacuum force by choosing the appropriate sized opening.

Figure 4:
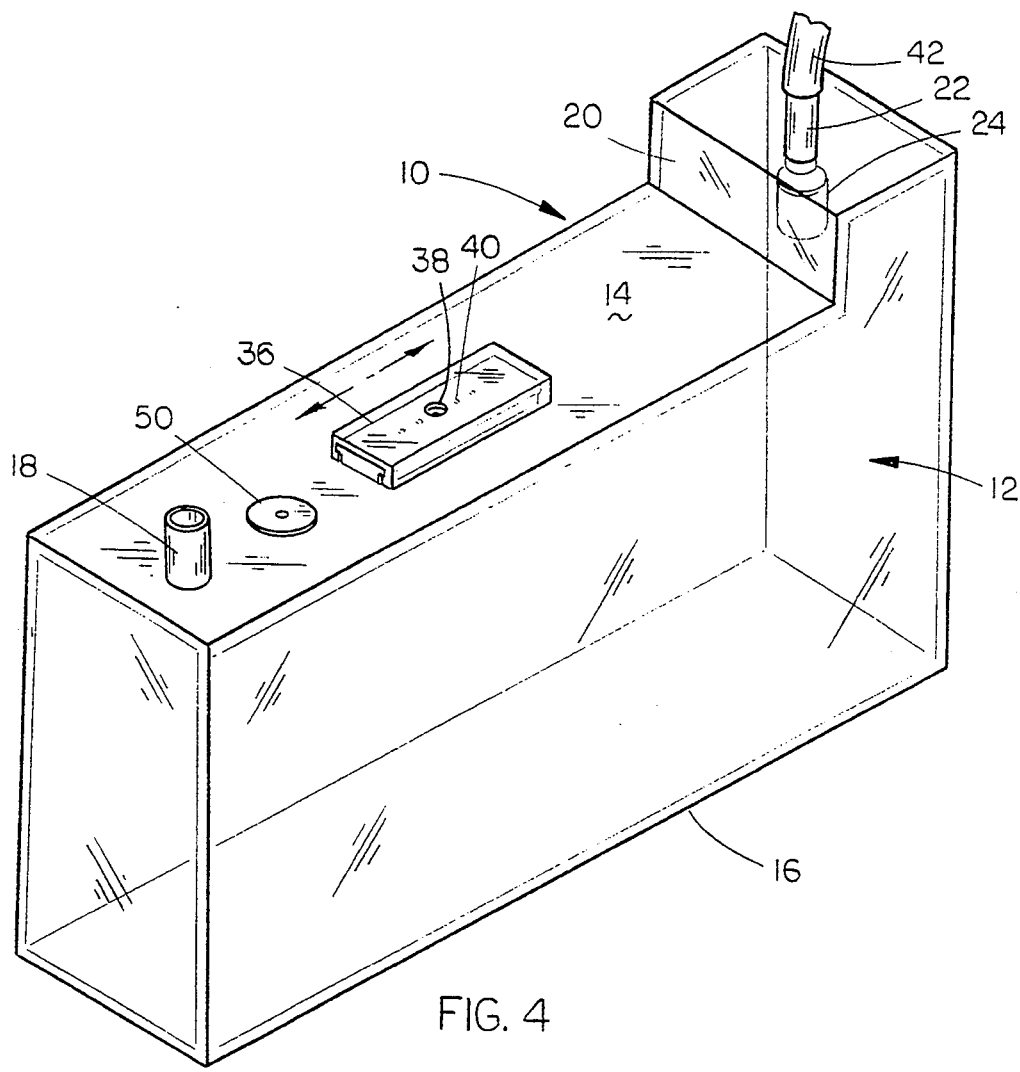
FIG. 4 is a perspective view of the apparatus showing two alternative embodiments of the vacuum control device.

Alternate embodiments are available with the vacuum control means. Rather than using a rotating vacuum control means, a sliding vacuum control means 36 is also available. Sliding vacuum control means 36 is rectangular in shape and is illustrated in FIG. 4. Instead of the openings formed in a circular fashion, the openings are formed in a straight line as shown by numeral 40 in FIG. 4. The principle operates in the same manner as in the rotational vacuum control means, but instead of rotating the opening, hole 38 slides over the various openings 40. By choosing the appropriately sized diameter opening to slide hole 38 over, the vacuum inside chamber 12 is controlled.

Figure 5:
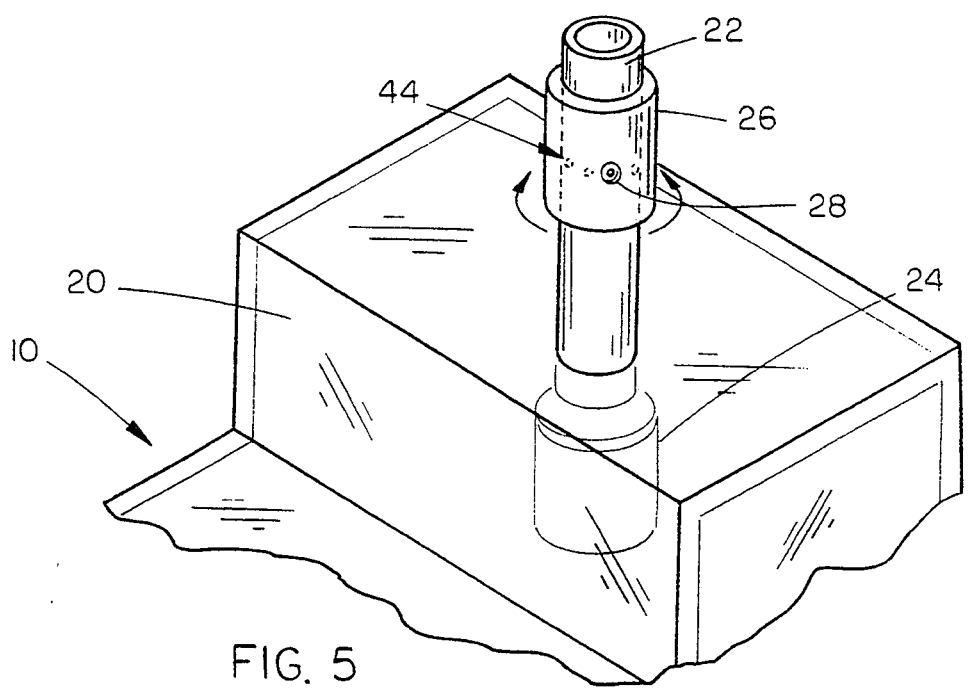
FIG. 5 shows the alternative vacuum control design of using openings formed in a catheter tube with a rotational cylindrical covering.

Another alternative embodiment for a vacuum control means is shown in FIG. 5. Instead of forming any openings in the collection chamber 12, the vacuum control means is formed within the catheter tube 42 which leads from port 22. This is illustrated in FIG. 5. The openings 44 are formed through the catheter tube 42 at a location above the port means 22. A rotational cylindrical covering 26 surrounds the catheter tube over the openings 44. A hole 28 is formed inside the rotational cylindrical covering and may be rotated over the openings 44 as desired. Again, the principle of controlling the vacuum force is the same as in the other embodiments.

In the event of vacuum pump failure in the closed position, air from the lung could build up pressure in the collection chamber to a level which could possibly collapse the lung. To prevent lung collapse, the relief or exhaust valve 50 is provided. When the positive pressure within the chamber reaches a predetermined level, exhaust valve 50 moves to the open position thereby preventing a pressure buildup within the storage chamber.

It can therefore be seen that the invention accomplishes at least all of its stated objectives.

I claim:

1. A thorax draining apparatus comprising, a collection chamber having upper and lower ends, opposite ends, and opposite sides, a chest catheter tube, said collection chamber having a first port means formed therein adjacent its upper end adjacent one end thereof which is fluidly connected to a vacuum pump for creating a negative pressure within said chamber, said collection chamber having a second port means formed therein adjacent its upper end adjacent its other end which is adapted to be connected to a chest catheter tube, said chamber having an exhaust port formed therein at its upper end, a first valve means in said collection chamber connected to said second port means which is movable between open and closed positions, said first valve means being in its open position during respiratory exhalation and being in its closed position during respiratory inspiration, said first valve means being positioned so as to discharge the contents of said chest catheter tube into said chamber adjacent the upper end of said chamber, a second valve means normally closing said exhaust port but which permits atmospheric communication of the upper interior of said chamber when a predetermined positive pressure is reached within said chamber, said chamber having a plurality of openings formed therein through its upper end, a selectively movable vacuum control means positioned above said plurality of openings for selectively controlling the negative pressure within said chamber, said vacuum control means comprising a cover member which is movably affixed to said upper end of said chamber and affixed directly above said plurality of openings in said chamber and capable of moving with respect to said upper end of said chamber, said cover member having a hole formed therein with said hole being formed in said cover member in a manner which permits said hole to be selectively aligned directly over one of said plurality of openings in said chamber, thus opening said chamber to the atmosphere, the selective movement of said cover member permitting a different opening in said chamber to be aligned directly under said hole in said cover member, the interior of said chamber being substantially unobstructed thereby providing direct flow between said first valve means and said first port means, whereby a substantially unobstructed air flow is permitted between said first valve means and said second port means.

2. The thorax drainage apparatus of claim 1 wherein each of said openings of said plurality of openings is circular in shape and wherein each of said openings has a different sized diameter.

3. The thorax drainage apparatus of claim 2 wherein said chamber has six openings located therein and the diameter of the openings are 0.052, 0.082, 0.070, 0.098, 0.110, and 0.128 inches in diameter, respectively.

4. The thorax drainage apparatus of claim 3 wherein said hole in said cover member has a diameter of 0.25 inches.

5. The thorax drainage apparatus of claim 2 wherein said cover member is circular in shape and as rotatably positioned over said plurality of openings in said chamber, said openings in said chamber are aligned in a circular fashion so that when said cover member is rotated about its axis any individual opening in said chamber may be lined up directly under said hole in said cover member.

6. The thorax draining apparatus of claim 2 wherein said cover member is rectangular in shape and is slidably movable back and forth over said plurality of openings of said chamber, said openings being aligned in a straight line in said chamber so that when said cover member slides back and forth, an individual opening in said chamber may be lined up directly under said hole in said cover member.

7. The thorax draining apparatus of claim 2 wherein said second port means comprises a vertically disposed cylindrical member having its upper end disposed above said upper end of said chamber and its lower end disposed within said chamber, and an access port in communication with the interior of said cylindrical member above said chamber and extending outwardly therefrom, and means selectively closing the outer end of said access port for permitting air to be selectively introduced into said chest catheter tube to relieve excess negative pressure in the chest catheter tube.

* * * * *